United States Patent
Chapman

(10) Patent No.: US 6,901,932 B2
(45) Date of Patent: Jun. 7, 2005

(54) RAPID DEPLOYMENT SOFT RESTRAINT APPARATUS AND METHOD

(75) Inventor: Bruce Chapman, Gardiner, NY (US)

(73) Assignee: Handle With Care, Inc., Gardiner, NY (US)

( * ) Notice: Subject to any disclaimer, the term of this patent is extended or adjusted under 35 U.S.C. 154(b) by 45 days.

(21) Appl. No.: 10/195,683

(22) Filed: Jul. 15, 2002

(65) Prior Publication Data

US 2003/0121525 A1 Jul. 3, 2003

Related U.S. Application Data

(63) Continuation-in-part of application No. 10/044,148, filed on Jan. 11, 2002.
(60) Provisional application No. 60/261,533, filed on Jan. 13, 2001.

(51) Int. Cl.[7] .................................................. A61F 5/37
(52) U.S. Cl. ....................... 128/878; 128/882; 128/876; 128/879; 2/312; 2/322
(58) Field of Search ............................... 128/878, 879, 128/882, 869, 876, 870; 2/312, 315, 316, 317, 318, 322, 338; 70/16

(56) References Cited

U.S. PATENT DOCUMENTS

| 4,854,138 | A | * | 8/1989 | Charland | 70/16 |
| 4,910,831 | A | * | 3/1990 | Bingold | 128/878 |
| 5,377,510 | A | * | 1/1995 | Smith | 70/16 |
| 5,651,376 | A | * | 7/1997 | Thompson | 128/878 |
| 5,797,404 | A | * | 8/1998 | Stanchin, II | 128/869 |
| 5,799,654 | A | * | 9/1998 | Kassan | 128/869 |
| 6,254,561 | B1 | * | 7/2001 | Borden | 128/882 |
| 6,446,474 | B1 | * | 9/2002 | Tabacchi et al. | 70/16 |
| 6,539,589 | B2 | * | 4/2003 | Thompson | 70/16 |

* cited by examiner

Primary Examiner—Fadi H. Dahbour
(74) Attorney, Agent, or Firm—Edward Etkin, Esq.

(57) ABSTRACT

An apparatus and method for rapidly restraining a person's limbs are disclosed. The inventive apparatus includes a pair of cuff modules, each with three rigid loops positioned on their outer surface, and a cuff interconnect having a flexible elongated body sized and configured to fit through the rigid loops, that is attached to one of the rigid loops on one of the cuff modules. When the cuff modules are applied to the person's limbs, the interconnect body is threaded through the other rigid loops and around the person's midsection, such that the interconnect body surrounds the person's midsection from front and back and forms two tension zones, one at each of the cuff modules to significantly restrict the range of motion of the person's first and second limbs. Optionally, the cuff modules may include releasable connectors to releasable connect to corresponding external stationary restraints. An optional additional set of two cuff modules with a second interconnect may be provided for securing the person's other limbs. The additional cuff module set and second interconnect is provided with a releasable connector for releasably connecting to an external restraint system.

30 Claims, 8 Drawing Sheets

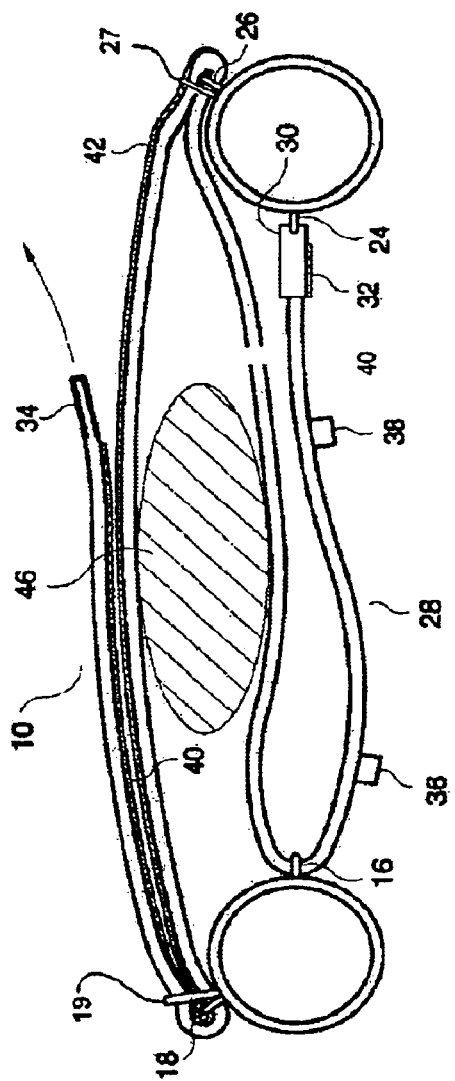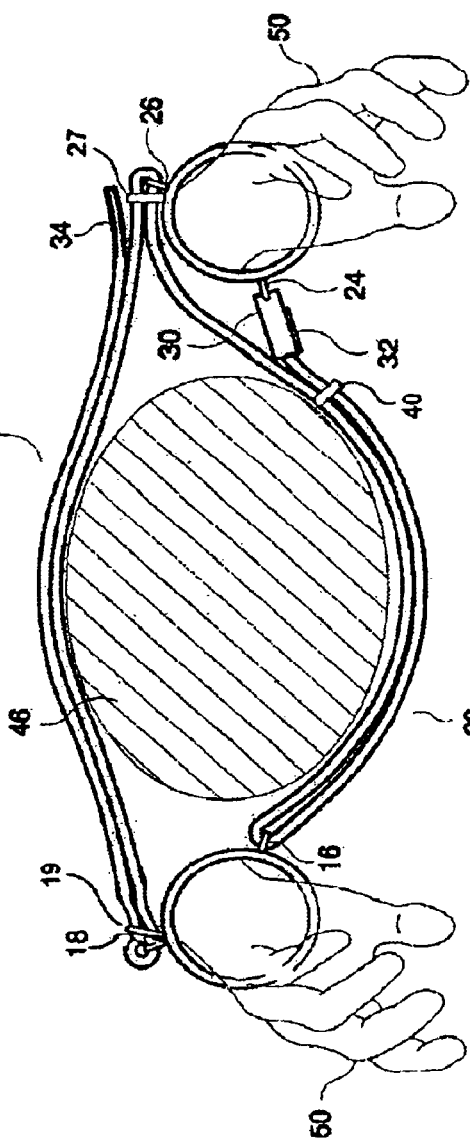

RAPID DEPLOYMENT SOFT RESTRAINT APPARATUS AND METHOD

REFERENCE TO PREVIOUSLY FILED APPLICATIONS

The present patent application is a continuation-in-part of a previously filed commonly assigned U.S. patent application Ser. No.: 10/044,148 entitled "Rapid Deployment Soft Restraint Apparatus and Method" filed on Jan. 11, 2002, which in turn claims priority from U.S. Provisional Patent Application Ser. No.: 60/261,533, entitled "Rapid Deployment Soft Restraint Apparatus and Method" filed on Jan. 13, 2001.

BACKGROUND OF THE INVENTION

The present invention is directed to a soft mechanical restraint system that may be easily and quickly deployed by a first person on a subject being held in a restrained position by a second person.

There are many thousands of human service and law enforcement agencies and facilities that provide care and supervision to aggressive, suicidal, and emotionally disturbed persons (hereinafter commonly referred to as "EDPs"). The staff and officers working in these agencies regularly come into physical contact with the EDPs through the use of physical subduing or restraint holds when the EDP becomes aggressive. Although there are many types of well-known physical subduing holds, the safest and most advantageous physical subduing hold is a Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON".

While restraint holds are useful for relatively short periods of time, often restraint of the EDP is necessary for an extended period. In such cases, the EDP must be restrained using some sort of a mechanical restraint system. Typically this involves placing wrist and ankle mechanical restraints on the EDP so that the EDP may be restrained for an extended period of time at the place of the restraint hold, or transported to another location while wearing the restraints. Most previously known restraint systems involve mechanical locks—for example, one popular restraint utilizes a mechanical spring-loaded lock that requires a special key to open. It takes at least 4–5 staff members to successfully apply such restraints at a speed of no lower than 2–3 minutes per restraint. During the application of these restraints, the EDP must be held down and poses a constant threat to the staff members until the restraining process is complete. Furthermore, removal of such restraints in emergency situations (i.e. in a medical emergency) takes a significant amount of time since a key must be located and used to open each restraint on each limb—this is especially problematic because without the key, which may not be immediately available in case of an emergency, the restraints cannot be removed at all. Finally, such complex restraint systems are expensive, heavy, and require extensive training to use properly.

Certain more recently developed restraints include mechanical locks based on a belt-like mechanism similar to a clothing belt with a buckle and a portion of the restraint having holes therein. Other similar restraints include a protruding metal member on one portion of the restraint and slots cut into the body of the restraint such that when the restraint is applied to the EDP, the portion with slots is pulled over the portion with the metal member until the restraint is tightened and the metal member is pushed through one of the slots. The end section of the slot portion may be further secured to the restraint. One of the main drawbacks with this arrangement is the fact that it is impossible to fit the restraint exactly to the hand or foot of the EDP since the restraint can only be tightened in increments equal to distance between the slots. As a result, it is possible that the restraint will be too loose (making it easier for the EDP to remove their limb from the restraint), or too tight (posing a danger of cutting off blood flow to the limb). Furthermore, a struggling unsupervised EDP may be able to loosen the restraint by pushing the slot portion of the restraint away from the metal member. Finally, all types of above restraints require special custom-made connectors to connect to one another or to stationary positions (i.e. a bed, etc.).

Manipulation of the previously known restraints once attached is difficult as well, requiring several people to pull webbing through complex system of buckles and connectors to connect cuff restraints to one another. And often, once an EDP is moved to a stationary restraint area, the restraints used during EDP transport must be removed and replaced with stationary restraints.

The above problems and challenges are at least partially advantageously solved by a novel circular cuff module that may be applied to each of an EDP's limbs quickly (and removed therefrom) by staff members without use of complex locking mechanisms as disclosed in a commonly assigned co-pending U.S. patent application entitled "Soft Circular Restraint Apparatus and Method" incorporated herein by reference in its entirety. Several advantageous approaches to interconnecting the novel cuff modules are disclosed as well.

However, one of the main challenges of previously known restraint systems, including the one disclosed in the above-incorporated "Soft Circular Restraint Apparatus and Method" patent application, is in how the cuff restraints are connected to one another. While connecting ankle cuff modules to one another by a simple interconnect may serve to prevent the EDP from kicking and to limit the EDP's walking speed, application of a simple wrist interconnect may pose a problem with particularly violent and/or aggressive EDPs. Similarly, while a simple wrist interconnect may prevent the EDP from using their hands independently from one another, the EDP is not prevented from flailing their arms at elbows and shoulders if the restrained wrists are at the EDP's front, and thus the EDP may still attack staff members even if the wrists are pulled together. Securing the EDP's wrists behind their back is a partial solution, but a nimble EDP can contort themselves to move their wrists to the front of their body. While some attempts have been made to develop more secure wrist interconnects, invariably these devices are cumbersome, heavy, and expensive to manufacture. Most importantly, the complexity of such devices require several staff members to apply them to EDPs. Unfortunately, this also means that such restraints are very difficult and time consuming to remove from the EDP in case of an emergency.

With respect to ankle restraints, while the novel circular cuff modules, disclosed in the above-incorporated patent application, include connectors to releasably connect to stationary connectors (such as may be disposed on a bed), other types of ankle modules and respective interconnects do not possess any mechanism to connect to stationary connectors.

Thus, it would be desirable to provide an apparatus and method for quickly and easily applying mechanical restraints to a person being controlled through a restraining hold or who is otherwise immobile. It would furthermore be desirable to provide a mechanical restraint apparatus that is comfortable to the subject and that may be quickly and easily removed in case of an emergency. It would additionally be desirable to provide a mechanical restraint system that severely restricts the range of motion of the person's arms. It would further be desirable to provide a mechanical restraint system that can be attached to commonly available stationary connectors. It would also be desirable to provide a lightweight mechanical restraint system that is easy to transport and use and that is inexpensive to manufacture. Moreover, it would be desirable to provide a mechanical restraint system that may be easily controlled by a single person during and after its application.

SUMMARY OF THE INVENTION

The apparatus of the present invention, and method of use thereof, remedies the problems associated with applying mechanical restraints to violent and/or struggling EDPs (and with removing the restraints therefrom). In brief summary, the inventive rapid deployment restraint apparatus advantageously provides: (1) quick and easy application to the EDP as well as quick and easy removal in case of an emergency; (2) severe restriction to the range of motion of the EDPs arms; (3) a secure fit to any EDP size as the inventive restraint apparatus is dynamically fitted exactly to the EDP size during application thereof; (4) optional easy attachment to commonly available stationary connectors, such as seat belt connectors; (5) lightweight and simple construction, making the inventive restraints easy to transport and use, and inexpensive to manufacture; and (6) easy control of the restraint apparatus by a single person during and after its application to the EDP.

The inventive apparatus includes an arm restraint system with a pair of cuff modules, each with three rigid loops positioned on their outer surface, and a first cuff interconnect having a first flexible elongated body, sized and configured to fit through the rigid loops, that is attached to one of the rigid loops on one of the cuff modules. When the cuff modules are applied to the EDP's wrists, the first body is threaded through the other rigid loops and around the EDP's midsection, such that the first body surrounds the EDP's midsection from front and back, such that when the first body is threaded through two loops on each cuff module and around the EDP's midsection, a tensioning arrangement is created that secures the first body around the EDP's midsection, such that the range of motion of the EDP's first and second limbs is significantly restricted. Optionally, the cuff modules may include releasable connectors to releasably connect to corresponding external stationary restraints.

An optional leg restraint system, that includes an additional set of two cuff modules and a second interconnect with second elongated body connecting the additional cuff modules to one another, may be provided for securing the EDPs ankles and restricting the motion of the EDPs legs. The leg restraint system is provided with a releasable connector positioned on the second body for releasably connecting to an external restraint system. Additional embodiments of the leg restraint system include releasable connectors for releasably connecting the second body to the additional cuff modules, and optional tensioning devices for controlling the length of the second body, and thus the distance between the additional cuff modules.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures:

FIG. 1C shows a side view of the arm restraint system of FIG. 1A in a second partial deployment position;

FIG. 1D shows a side view of the arm restraint system of FIG. 1A in a fully deployed position restraining a person's arms next to the person's waist;

DESCRIPTION OF THE PREFERRED EMBODIMENTS

Figure 1A:
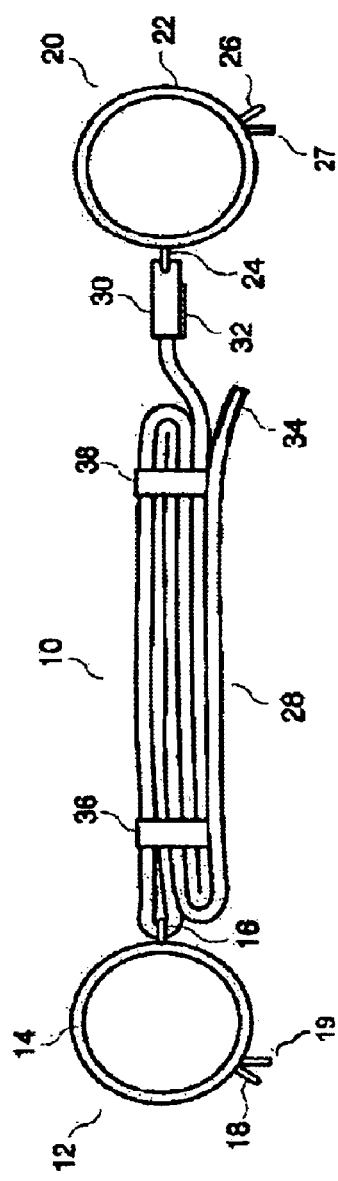
FIG. 1A shows a side view of an arm restraint system of the present invention in a storage position.

The present invention relates to an advantageous soft mechanical restraint apparatus and method that may be quickly and easily applied by a first person to a subject being held in a restraining hold by a second person, or to a subject who is otherwise immobilized (e.g. unconscious, sedated, asleep, etc.).

It should be understood that while the present invention refers to Emotionally Disturbed Persons (hereinafter "EDPs") and staff members, the inventive techniques and apparatus may be applied in virtually any situation where a subject is being restrained and application of mechanical restraints is warranted. Thus, the present invention is applicable in law enforcement, hospitals, mental health care facilities, drug and alcohol rehabilitation centers, etc.

Before application of any sort of mechanical restraints, it is important that control over a struggling EDP is established by placing the EDP into a restraining hold. The Primary Restraint Technique (hereinafter "PRT") is an advantageous modular single person restraint that is applied by an EDP care professional (hereinafter "staff member") to an EDP from behind. The maneuvers involved in implementing the PRT are described in greater detail in Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON" which is hereby incorporated by reference in its entirety. It should be noted however that the restraint system of the present invention does not require use of the PRT—it may be advantageously be utilized in any situation where the EDP is physically restrained by one or more staff members or other individuals. Of course if the EDP is not ambulatory (i.e. unconscious or asleep), it is not necessary to apply any restraint holds before application of the inventive restraint apparatus.

In summary, the restraint apparatus of the present invention comprises an arm restraint system with a cuff module for each wrist, and a flexible first interconnect for connecting the wrist cuff modules to one another, and a leg restraint system with a cuff module for each ankle and a flexible second interconnect for connecting the ankle cuff modules to one another. It should be understood to one skilled in the art that the arm and leg restraint systems can be readily utilized independently from one another without departing from the spirit of the invention. For example, in certain situations only the arm restraint system may be used, while in another situation, only the leg restraint system may be utilized.

Furthermore, while the arm and leg restraint systems of the inventive apparatus are described below and shown in the drawings as applied to arms and legs respectively, it should be apparent to one skilled in the art that the arm restraint system can be applied to the EDP's legs and the leg restraint system can be applied to the EDPs arms without departing from the spirit of the present invention. The key factor in such an application of the restraint apparatus is the size of the cuff modules. So if the first interconnect is to be used to secure the EDP's legs, it should be connected to ankle-sized cuff modules, similarly, if the second interconnect is to be used to secure the EDP's arms, it should be connected to wrist-sized cuff modules.

It should be noted that all directions of how cuff module interconnects are threaded through, and connected to, various elements of the cuff modules, are shown and described by way of example only and may be easily be reversed without departing from the spirit of the invention.

Referring now to FIG. 1A, an arm restraint system 10 is shown in a storage/transport configuration. The arm restraint system 10, includes a first cuff module 12, a second cuff module 20 and an interconnect 28 therebetween. Preferably, the cuff modules 12 and 14 are those described in the co-pending commonly assigned U.S. patent application entitled "Soft Circular Restraint Apparatus and Method", which is hereby incorporated by reference in its entirety, but modified with two additional rigid loops added proximal to one of the rigid loops on each cuff module. The cuff modules from the above-incorporated "Soft Circular Restraint Apparatus and Method" patent application, and their utilization with the inventive arm restraint system 10 are described in greater detail below in connection with FIGS. 3A and 3B.

However, the arm restraint system 10 may be utilized with a set of any other generally circular cuff modules (for example, any commercially available resilient cuff restraints) as long as each cuff module includes (or is modified to include) three rigid loops on its outer surface positioned apart from one another when the cuff module is in a closed or deployed position as described below. It should be noted that the cuff modules 12, 20 are shown in simplified views in the various figures and may include additional elements (such as locking mechanisms) that are not shown in the figures because such additional elements are not relevant to the present invention. Moreover, the additional pair of rigid loops may be placed away from the other rigid loop without departing from the spirit of the invention.

Furthermore, while the various embodiments of the inventive restraint apparatus are described with references to particular hook and loop material strips positioned on various portions of the inventive first and second interconnects, any loop and hook material strips may be interchanged between one another throughout the first and second interconnects, as long as the interchange is consistent overall, as a matter of design choice.

A first rigid loop 16 is positioned perpendicular to an outer surface of a cuff body 14 of the cuff module 12. The rigid loop 16 is preferably generally rectangular and composed of a strong material such as metal, hard plastic, or metal coated with a resilient material. The opening in the rigid loop 16 is sized and configured to allow the interconnect 28 to readily pass therethrough. Preferably, the rigid loop 16 has a limited range of pivoting motion about its lower portion by which it is attached to the cuff body 14, however, the rigid loop 16 may also be secured in a non-movable, or a very limited pivot position perpendicular to the cuff body 14.

A pair of rigid loops 18, 19 are positioned perpendicular to the top surface of the cuff body 14 at a first predetermined distance away from the rigid loop 16. The rigid loops 18, 19 are preferably identical to the rigid loop 16, being generally rectangular and composed of a strong material such as metal, hard plastic, or metal coated with a resilient material. The openings in the rigid loops 18, 19 are sized and configured to allow the interconnect 28 to readily pass therethrough in a tensioning configuration. Preferably, the rigid loops 18, 19 have a limited range of pivoting motion about their lower portions by which they are attached to the cuff body 14. However, the rigid loops 18, 19 may also be secured in a non-movable or a very limited pivot position perpendicular to the cuff body 14. The first predetermined distance between the rigid loops 16, and 18, 19 may be selected as a matter of design choice, but is preferably approximately between one third to one half of the external circumference of the cuff body 14.

A rigid loop 24 is positioned perpendicular to an outer surface of a cuff body 22 of the cuff module 20. The rigid loop 24 is preferably generally rectangular and composed of a strong material such as metal, hard plastic, or metal coated with a resilient material. The opening in the rigid loop 24 is sized and configured to allow the interconnect 28 to readily pass therethrough. Preferably, the rigid loop 24 has a limited range of pivoting motion about its lower portion by which it is attached to the cuff body 22, however the rigid loop 24 may also be secured in a non-movable or a very limited pivot position perpendicular to the cuff body 22.

A pair of rigid loops 26, 27 is positioned perpendicular to the top surface of the cuff body 22 at the first predetermined distance away from the rigid loop 24, The rigid loops 26, 27 are preferably identical to the third rigid loop 24, being generally rectangular and composed of a strong material such as metal, hard plastic, or metal coated with a resilient material. The openings in the rigid loops 26, 27 are sized and configured to allow the interconnect 28 to readily pass therethrough. Preferably, the rigid loops 26, 27 have a limited range of pivoting motion about their lower portion by which they is attached to the cuff body 22. However, the rigid loops 26, 27 may also be secured in a non-movable or a very limited pivot position perpendicular to the cuff body 22. The first predetermined distance between the rigid loops 24 and 26, 27 may be selected as a matter of design choice but is preferably approximately one third to one half of the external circumference of the cuff body 22.

Figure 1B:
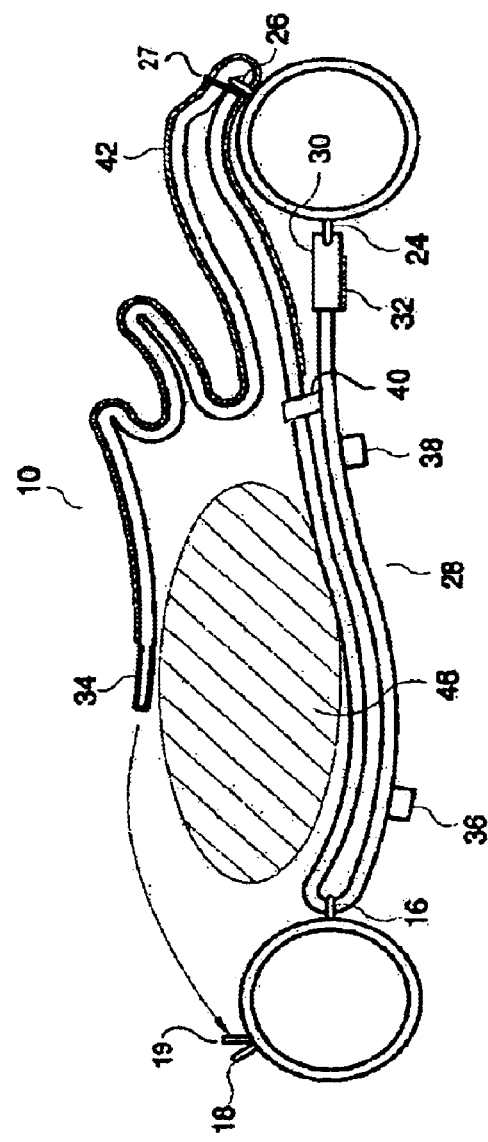
FIG. 1B shows a side view of the arm restraint system of FIG. 1A in a first partial deployment position.
Figure 1E:
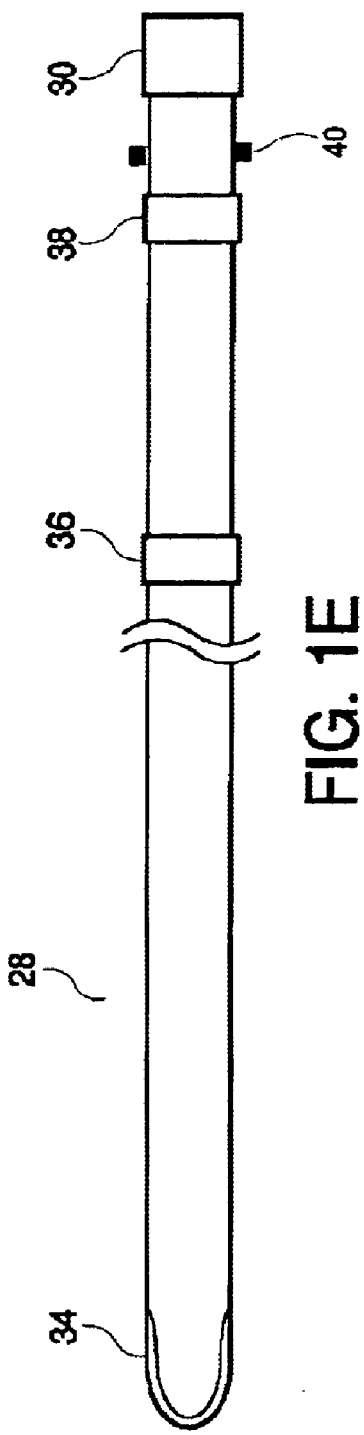
FIG. 1E shows a bottom view of an interconnect portion of the arm restraint system of FIG. 1A.
Figure 1F:
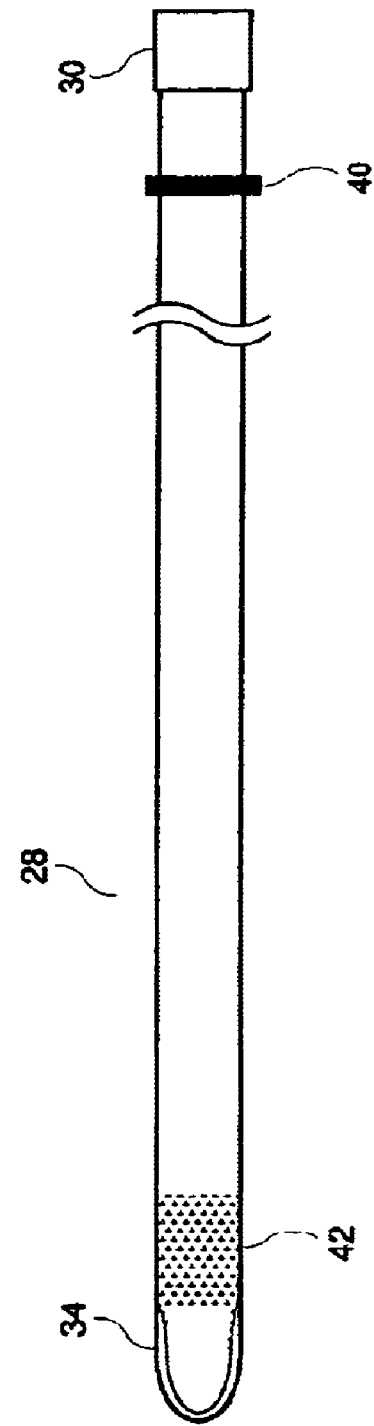
FIG. 1F shows a top view of the interconnect portion of FIG. 1E.

Referring now to FIGS. 1E and 1F, the interconnect 28 is shown from a bottom view (FIG. 1E) and a top view (FIG. 1F). The interconnect 28 is an elongated body composed of a strong flexible material such as nylon webbing (for example, of the type used in seat belts and parachute straps) with a top surface and a bottom surface, a first end and a second end. The interconnect 28 includes a connector 30 for connection to one of the rigid loops of the cuff modules 12, 20 at the first end and an optional stiffening element 34 positioned on its second end. The interconnect 28 also includes a rigid loop 40 positioned perpendicularly to its surface, such that when the system 10 is deployed, the rigid loop 40 is proximal to an EDP's midsection side.

The connector 30 may be a simple loop of a portion of the interconnect 28 pulled through one of the rigid loops of the cuff modules 12, 20 and secured to itself, or another configuration of a permanent connector that connects to one of the rigid loops. Optionally, the connector 30 may be a releasable connector that enables the first end of the interconnect 28 to be releasably connected to one of the rigid loops of the cuff modules 12, 20. Any known configuration of a releasable connector may be used. A novel embodiment of a connector 30 that may be advantageously used as a releasable connector with the interconnect 28 is described below in connection with FIGS. 2A to 2C.

The stiffening element 34 may be composed of additional webbing, plastic lining, or another resilient material. While the stiffening element 34 is not essential, it serves to facilitate threading of the interconnect 28 through the various rigid loops of the cuff modules 12, 20.

Optionally, a loop material strip 42 (such as loop Velcro®) is positioned on the top surface of the interconnect 28 near the stiffening element 34 The loop material strip 42 is preferably a small strip approximately as wide as the interconnect 28. An optional hook material strip 32 (such as hook Velcro®) may be positioned either on top or on bottom of the connector 30 for releasably connecting to a portion of the loop material strip 42 if the second end of the interconnect 28 is brought into contact with the connector 30 after it is folded. While the above elements 32 and 42 are described with reference to either hook or loop material, it should be understood to one skilled in the art that any other flexible releasable attachment devices can be readily substituted for the hook and loop material without departing from the spirit of the invention. For example, the elements 32, 42 may be replaced with releasable glue strips or the like.

The interconnect 28 also includes optional elastic loops 36 and 38 disposed between the first end and the loop material strip 42, and preferably closer to the first end. The elastic loops 36 and 38 may be composed of resilient elastic webbing, rubber or similar material, and either encompass a central axis of the interconnect 28 and thus freely slide along the interconnect 28, or are secured to either the top or the bottom surface of the interconnect 28 (as shown in FIGS. 1A, 1B, 1C and 1E) as a matter of design choice without departing from the spirit of the invention. Furthermore, either a single elastic loop or three or more elastic loops may be positioned on the interconnect 28 and used as a matter of design choice without departing from the spirit of the invention.

Returning now to FIG. 1A, to place the arm restraint system 10 in a storage/transport position, the interconnect 28 is attached to the rigid loop 24 of the cuff module 20 via the connector 30, extended toward the rigid loops 18, 19 of the cuff module 12 and threaded through one or both loops 18, 19. The interconnect 28 is then folded back upon itself several times and secured in the folded state by the elastic loops 36 and 38. The amount of times the interconnect 28 is folded upon itself depends on the desired distance between the cuff modules 12, 20 during storage/transport. Thus, if the cuff modules 12, 20 are to be close to one another, the interconnect 28 should be folded several times. The hook and loop material strips 32, 42 serve to further secure the interconnect 28 in the storage position.

Referring now to FIGS. 1B to 1D, the deployment of the arm restraint system 10 is shown in three stages. Referring to FIG. 1B, the arm restraint system 10 is released from the storage/transport configuration (shown in FIG. 1A) and pulled apart such that the interconnect 28 is threaded through the rigid loop 16 of the cuff module 12 from bottom to top and folded back upon itself extending toward the cuff module 20 and threaded again through the rigid loop 40. The rigid loop 40 creates a comfort zone for the restrained EDP by preventing the interconnect 28 from impacting the side of EDP's body 46 during the deployment of the system 10.

Preferably, before deployment on the EDP, the interconnect 28 is threaded straight through the rigid loops 26, 27 and readily pulled (or let out) to adjust the distance between the cuff modules 12, 20 to a desired value. This value depends on the width of the EDP's body 46. If the body 46 is wide, the distance between the cuff modules 12, 20 should be greater than when the body 46 is narrow. The preferred method of application of the arm restraint system 10 is when the EDP is restrained face-down on a floor surface and is under control of a staff member (or when the EDP is sedated, asleep or unconscious and may be readily placed in a face-down position). The PRT system of the above-incorporated U.S. Pat. No. 6,273,091 patent is ideal for preparing the EDP for application of the arm restraint system 10 because one of the PRT positions involves placing the EDP face-down on a floor surface in a controlled hold.

However, the application of the arm restraint system 10 is described with reference to the EDP being face down on a floor surface by way of example only. It should be understood that the arm restraint system 10 may be applied to an EDP being face-up on the floor or in a standing position, as long as the EDP is immobilized during the application thereof, without departing from the spirit of the invention.

Referring now to FIG. 1C, once the EDP is immobilized, the cuff module 20 is applied to one of EDP's wrists 50 (as shown in FIG. 1D) and the cuff module 12, along with a portion of the interconnect 28 that is between the cuff modules 12, 20, is passed under the EDP's body 46. The cuff module 12 is then secured to the EDP's other wrist 50, and then the interconnect 28 is pulled (through the rigid loops 40, 26, and 27) to bring the EDP's wrists 50 closer to the EDP's body 46. The interconnect 28 is then folded back upon itself and threaded through the rigid loop 26 (thereby forming a first tensioning mechanism with the rigid loops 26, 27) before being passed over the top of the body 46 and threaded straight through the rigid loops 18 and 19 from right to left. The interconnect 28 is then pulled through the rigid loops 18, 19 until the EDP's wrists 50 are in tight contact with the sides of the EDP's body 46, and then folded back upon itself and threaded through the rigid loop 19 (thereby forming a second tensioning mechanism with the rigid loops 18, 19) to extend over the EDP's body 46 in the direction of the cuff module 20, where optionally it may be tucked behind its section extending fully over the body 46. The two tensioning mechanisms secure the cuff modules 12, 20 to the sides of the body 10 and prevent the EDP from being able to slide the cuff modules 12, 20 along the interconnect 28.

As described above, the deployment of the arm restraint system 10 is quick and easy. Because of the advantageous construction and method of application of the inventive arm restraint system 10, the EDP has no leverage to move their arms. Advantageously, in case of an emergency, the arm restraint system 10 can be easily released by pulling on the second end of the interconnect 28 to detach the first loop material strip 40 from the first hook material strip 42, and threading the interconnect 28 back through the rigid loop 18 (and optionally through the rigid loop 26) to completely release the EDP's arms.

The lightweight inventive arm restraint system 10 can withstand approximately 10,000 pounds of force, all without any metal key elements. This is due to the fact that the circular nature of the deployment and tensioning of the interconnect 28 through rigid loop pairs makes all EDP's movements self-canceling—i.e. when the EDP pulls on one cuff module, the tension on the other cuff module is increased proportionally. Because all elements of the arm restraint system 10 are resilient, the EDP will not hurt themselves or experience significant discomfort by struggling against the system 10. It takes less than 25 seconds for a single person to deploy the arm restraint system 10 from its storage position (shown in FIG. 1A) to its deployed restraint position (FIG. 1D) Most importantly, the arm restraint system 10 can be easily released in one second in an emergency situation without need for a special key.

Figure 2A:
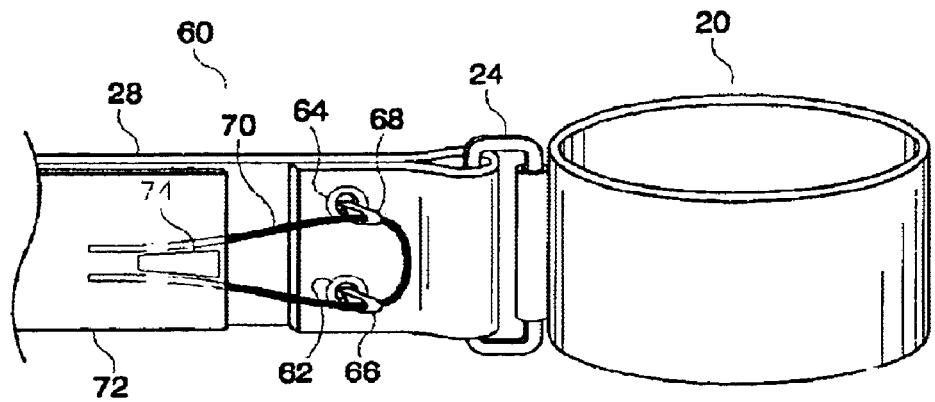
FIG. 2A shows an isometric top view of a releasable connector, in a closed position, for releasably connecting the interconnect portion of FIG. 1D to one of the cuff modules of the arm restraint system of FIG. 1A.
Figure 2B:
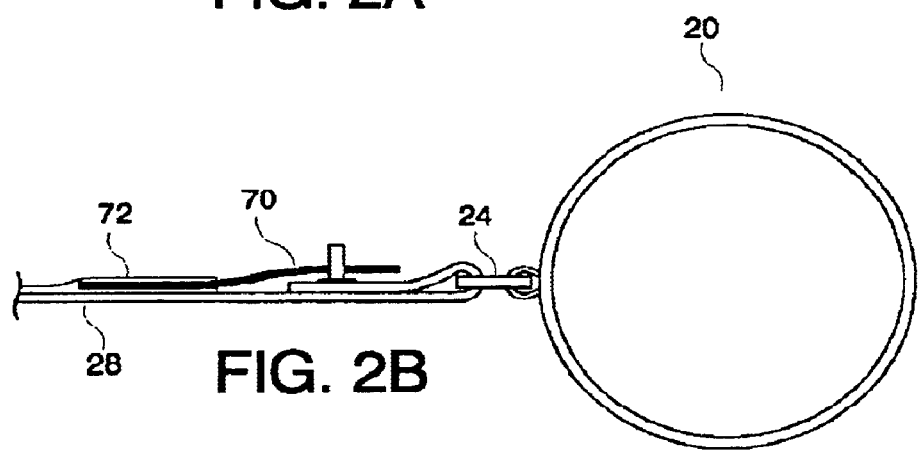
FIG. 2B shows a side view of the releasable connector of FIG. 2A in the closed position.
Figure 2C:
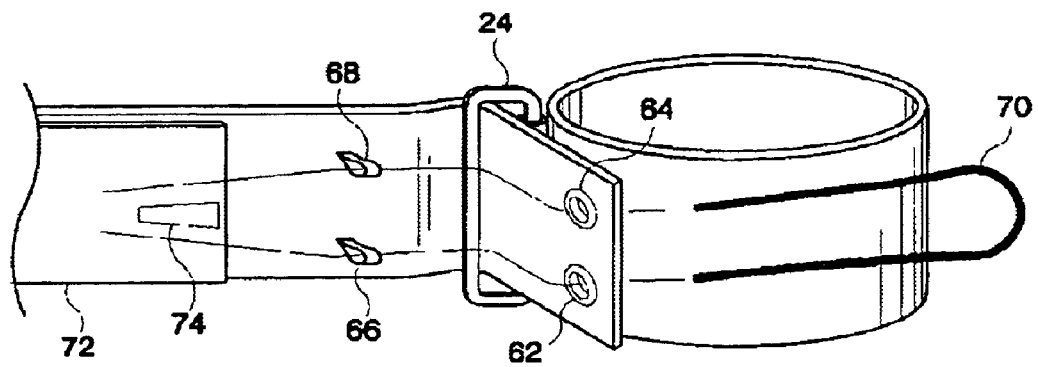
FIG. 2C shows an isometric top view of the releasable connector of FIG. 2A in an open position.

Referring now to FIGS. 2A to 2C, an exemplary embodiment of the connector 30 is shown as a releasable connector 60. The releasable connector 60 includes a first elongated loop 66 positioned perpendicular to the top surface of the interconnect 28 at a predetermined distance from the first end of the interconnect 28, and a second elongated loop 68, positioned next to the elongated loop 66 and perpendicular to the top surface of the interconnect 28, at the same predetermined distance away from the first end. The elongated loops 66, 68 may be composed of wire, plastic or an elastic material. The releasable connector 60 also includes a first hole 62 defined proximal to the first end, and a second hole 64, next to the hole 62, also defined proximal to the first end, the holes 62, 64 being positioned and sized such that when the first end of the interconnect 28 is threaded through the rigid loop 24 from bottom to top and then folded upon itself, the holes 62, 64 are aligned with the respective elongated loops 66, 68, such that the elongated loops 66, 68 pass through the respective holes 62, 64 to thereby at least temporarily connect the first end of the interconnect 28 to the rigid loop 24. The holes 62, 64 may optionally be reinforced with rings (for example made from metal or plastic) as shown in FIGS. 2A–2C.

The releasable connector 60 further includes a generally "U-shaped" connection element 70 having two segments, each sized and configured to fit though a respective elongated loop 66, 68, once the elongated loops 66, 68 are passed through the respective holes 62, 64. The connection element 70 may be any strong thin material such as a wire or a hard plastic. Optionally, the connection element 70 may be coated with a resilient material to facilitate passage through the elongated loops 66, 68.

A retaining device 72, positioned proximal to the elongated loops 66, 68, receives and retains the first and second segments of the connection element 70 after they are passed through the elongated loops 66, 68. The retaining device 72 may be a cloth, plastic, or metal pocket attached to the top surface of the interconnect 28. An optional guide 74, such as a plastic, metal, or cloth member may be positioned centrally inside the retaining device 72 to guide the first and second segments of the connection element 70 into the retaining device 72. The releasable connector 60 is shown in a closed "connected" position in FIGS. 2A and 2B, and in an open "released" position in FIG. 2C.

Figure 3A:
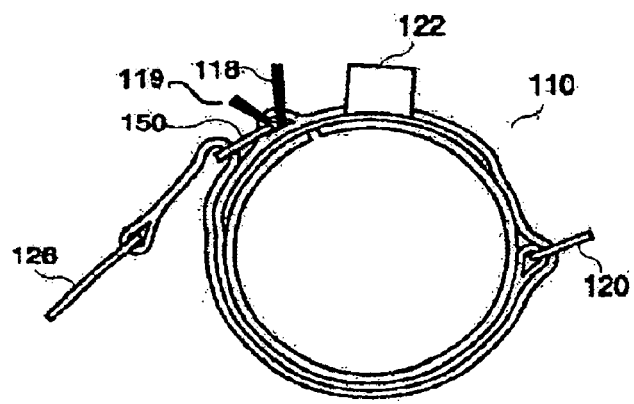
FIG. 3A shows a side view of an alternate embodiment of a cuff module of the arm restraint system of FIG. 1A.
Figure 3B:
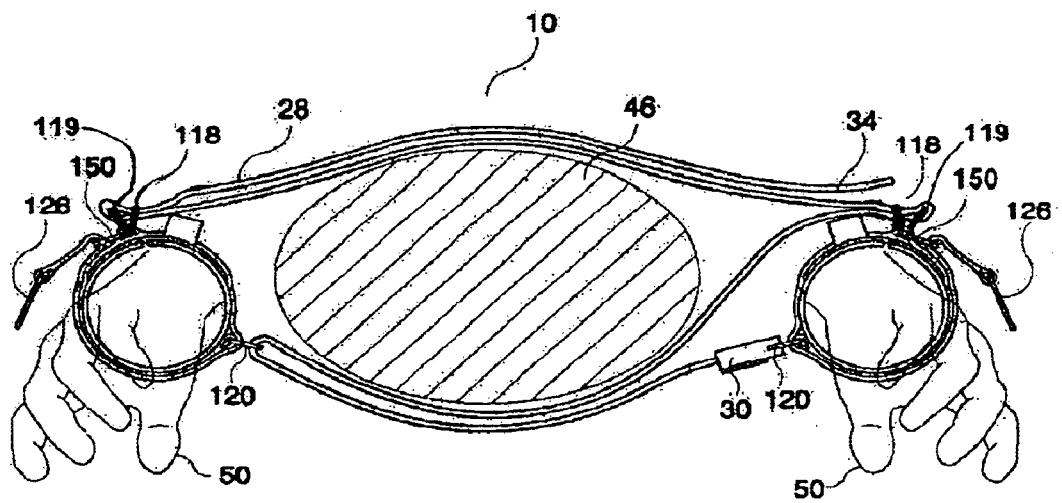
FIG. 3B shows the cuff modules of FIG. 3A utilized in the arm restraint system of FIG. 1A.

As discussed before, the soft circular cuff modules from the above-incorporated "Soft Circular Restraint Apparatus and Method" patent application (hereafter "circular cuff modules") may advantageously be utilized in the arm restraint apparatus 10. Referring now to FIG. 3A, a simplified view of a circular cuff module 110 is shown. The basic operation of the circular cuff module 110 involves placing it around an EDP's wrist and then threading a portion of the circular cuff module 110, terminating in a rigid connector 126, first through a rigid loop 120 and then through a rigid loop 150. Advantageously, the rigid connector 126 may be connected to an external stationary restraint system (not shown). The circular cuff module 110 is identical to the circular cuff module from the "Soft Circular Restraint Apparatus and Method" patent application, except that an additional pair of rigid loops 118, 119 is added next to the rigid loop 150. Thus, the rigid loop 120 may used equivalently to the rigid loop 16 or the rigid loop 24 of the cuff modules 12, 20 respectively, while the rigid loops 118, 119 may used equivalently to the rigid loops 18, 19 or the rigid loops 26, 27 of the cuff modules 12, 20 respectively. Referring now to FIG. 3B, the restraint apparatus 10 is shown as deployed around the EDP's body 46 utilizing the circular cuff modules 110. Advantageously, the rigid connectors 126 may be used to secure the restrained EDP to an external stationary restraint system (not shown).

Figure 4A:
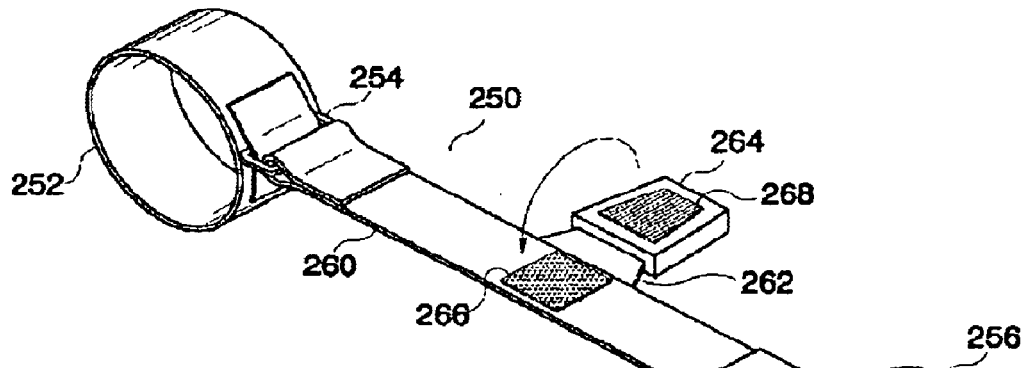
FIG. 4A shows an isometric top view of a first embodiment of a leg restraint system of the present invention.
Figure 4B:
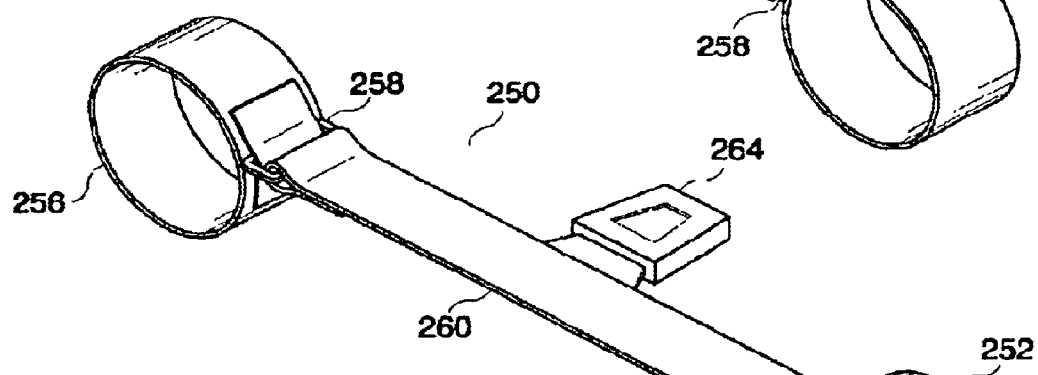
FIG. 4B shows an isometric bottom view of the first embodiment of the leg restraint system of FIG. 4A.
Figure 4C:
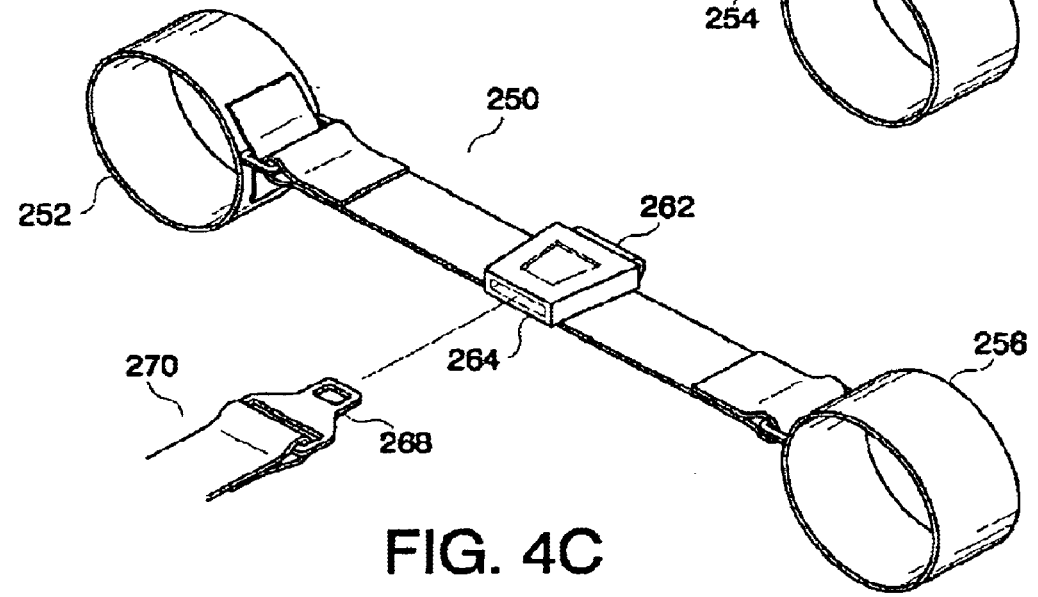
FIG. 4C shows an isometric top view of the first embodiment of the leg restraint system of FIG. 4A, readied for attachment to an external restraint connector.

Referring now to FIGS. 4A–4C, a first embodiment of a leg restraint system 250 of the present invention is shown. The leg restraint system 250, includes a first cuff module 252, a second cuff module 256, and an interconnect 260 therebetween. Preferably, the cuff modules 252 and 256 are similar to the circular cuff module 110 shown in FIG. 3A (and described in greater detail in the above incorporated "Soft Circular Restraint Apparatus and Method" patent application), except that the rigid loop 150 is not necessary.

However, the leg restraint system 250 may be utilized with a set of any other generally circular cuff modules (for example, any commercially available resilient cuff restraints) capable of connecting to an interconnect device. It should be noted that the cuff modules 252, 256 are shown in simplified views in the various figures, and may include additional elements (such as locking mechanisms) that are not shown in the figures because such additional elements are not relevant to the present invention.

The interconnect 260 has its first end connected to a rigid loop 254 disposed on an outer surface of the cuff module 252, and its second end connected to a rigid loop 258 disposed on an outer surface of the cuff module 256. Optionally, the interconnect 260 may be attached to the cuff modules 252, 256 in another manner. The length of the interconnect 260 may be selected as a matter of design choice. For example, if it is very short, the EDP will be unable to walk, while if it is long, the range of motion of EDP's legs will not be sufficiently restricted. In another example, the length of the interconnect 260 may be just sufficient for the EDP to walk in very small steps while being escorted by a staff member.

A releasable connector 264 is preferably attached perpendicular to one of the sides of the restraint interconnect 260 via a short strip 262. Preferably, the short strip 262 is positioned at a midpoint of the restraint interconnect 260 between the cuff modules 252, 256. The releasable connector 264 is configured to connect to an external stationary restraint system, shown as an external interconnect 270, having a connector 268 adapted for releasable connection to the connector 264. For example, the releasable connector 264 may be a female seat-belt type connector while the connector 268 may be a male seat-belt type connector. The strip 262 enables the releasable connector 264 to pivot in any direction perpendicular to the interconnect 260. A optional loop material strip 266 may be positioned on the interconnect 260 surface proximal to the short strip 262 and a hook material strip 268 may be positioned on a portion of the releasable connector 264 to releasably secure, via releasable connection with loop material strip 266, the releasable connector 264 to the interconnect 260 when the external interconnect 270 is connected thereto.

Figure 4D:
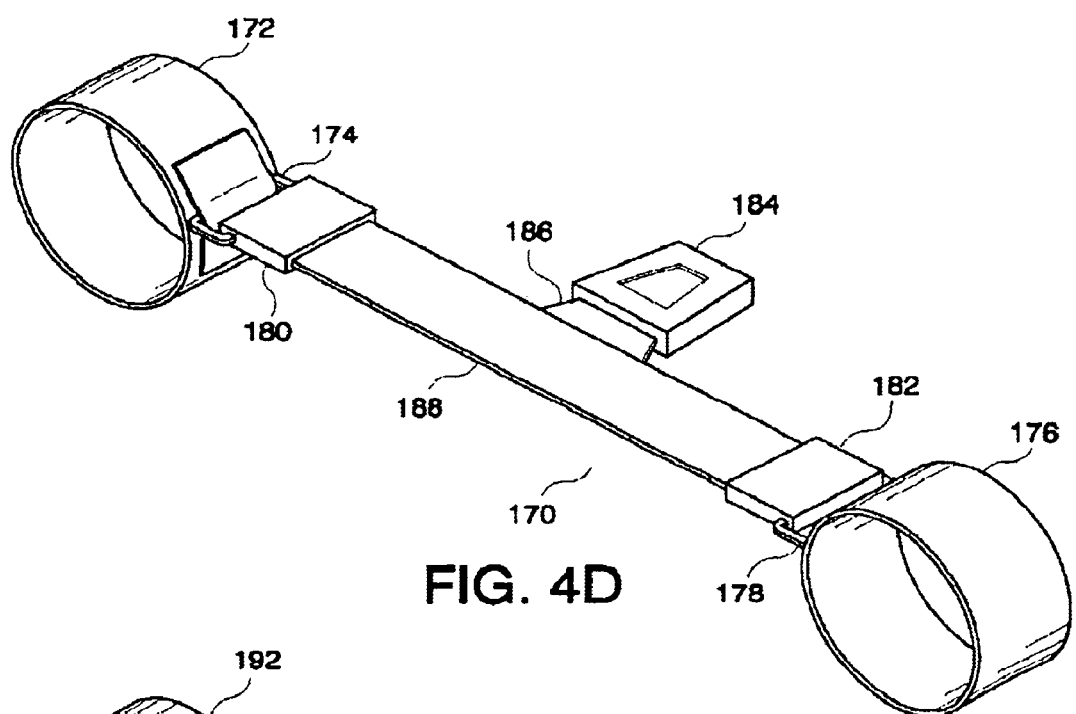
FIG. 4D shows an isometric top view of a second embodiment of a leg restraint system of the present invention.

Referring now to FIG. 4D, a second embodiment of the leg restraint system 250 of the present invention is shown as a leg restraint system 170. The leg restraint system 170, includes a first cuff module 172, a second cuff module 176, and an interconnect 188 therebetween. Preferably, the cuff modules 172 and 176 are similar to the circular cuff module 110 shown in FIG. 3A (and described in greater detail in the above incorporated "Soft Circular Restraint Apparatus and Method" patent application), except that the rigid loop 150 is not necessary.

However, the leg restraint system 170 may be utilized with a set of any other generally circular cuff modules (for example, any commercially available resilient cuff restraints) capable of connecting to an interconnect device. It should be noted that the cuff modules 172, 176 are shown in a simplified view and may include additional elements (such as locking mechanisms) that are not shown because such additional elements are not relevant to the present invention.

The interconnect 188 includes a first releasable connector 180 at its first end for releasable connection to the cuff module 172 via a rigid loop 174 disposed on the outer surface of the cuff module 172, and a second releasable connector 182 at its second end for releasable connection to the cuff module 176 via a rigid loop 178 disposed on the outer surface of the cuff module 176. The releasable connectors 180, 182 enable the interconnect 188 to be quickly disconnected from one or both cuff modules 172, 176 in case of an emergency without removing the cuff modules 172, 176 from the EDP's ankles. A third releasable connector 186 for attachment to an external restraint system (not shown) is attached to the interconnect 188 by a short strip 186. Other than the releasable connectors 180, 182, the leg restraint system 170 is substantially identical in construction and operation to the leg restraint system 250.

Figure 4E:
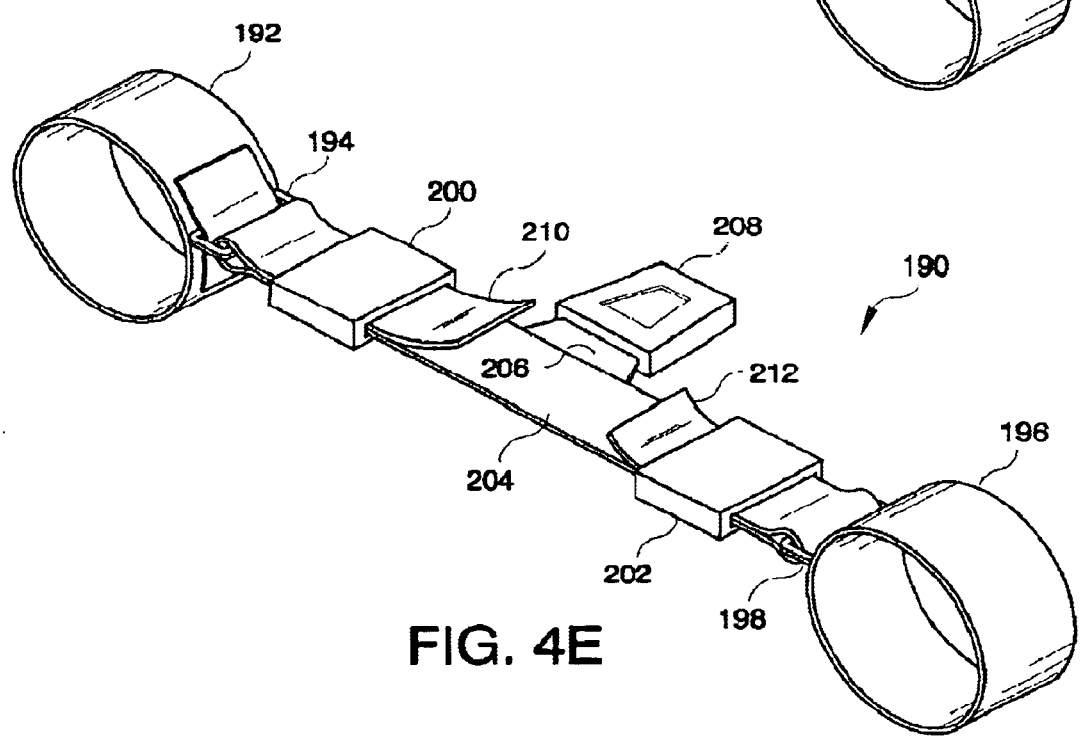
FIG. 4E shows an isometric top view of a third embodiment of a leg restraint system of the present invention.

Referring now to FIG. 4E, a third embodiment of the leg restraint system 250 of the present invention is shown as a leg restraint system 190. The leg restraint system 190 includes a first cuff module 192, a second cuff module 196, and an interconnect 204 therebetween. Preferably, the cuff modules 192 and 196 are similar to the circular cuff module 110 shown in FIG. 3A (and described in greater detail in the above incorporated "Soft Circular Restraint Apparatus and Method" patent application), except that the rigid loop 150 is not necessary.

However, the leg restraint system 190 may be utilized with a set of any other generally circular cuff modules (for example, any commercially available resilient cuff restraints) capable of connecting to an interconnect device. It should be noted that the cuff modules 192, 196 are shown in a simplified view and may include additional elements (such as locking mechanisms) that are not shown because such additional elements are not relevant to the present invention.

The interconnect 204 has its first portion connected to a rigid loop 194 disposed on an outer surface of the cuff module 192, and its second portion connected to a rigid loop 198 disposed on an outer surface of the cuff module 196. Optionally, the interconnect 204 may be attached to the cuff modules 192, 196 in another manner. The length of the interconnect 204 may be controlled by tensioning devices 200, 202 disposed thereon by pulling on one or both of the respective first end 210 and second end 212 of the interconnect 204. Optionally, only one of the tensioning devices 200, 202 may be provided. A releasable connector 208 for attachment to an external restraint system (not shown) is attached to the interconnect 204 by a short strip 206. Other than the tensioning devices 200, 202 (and the interconnect 204 ends 210, 212 pulled therethrough), the leg restraint system 190 is substantially identical in construction and operation to the leg restraint system 250.

Figure 5:
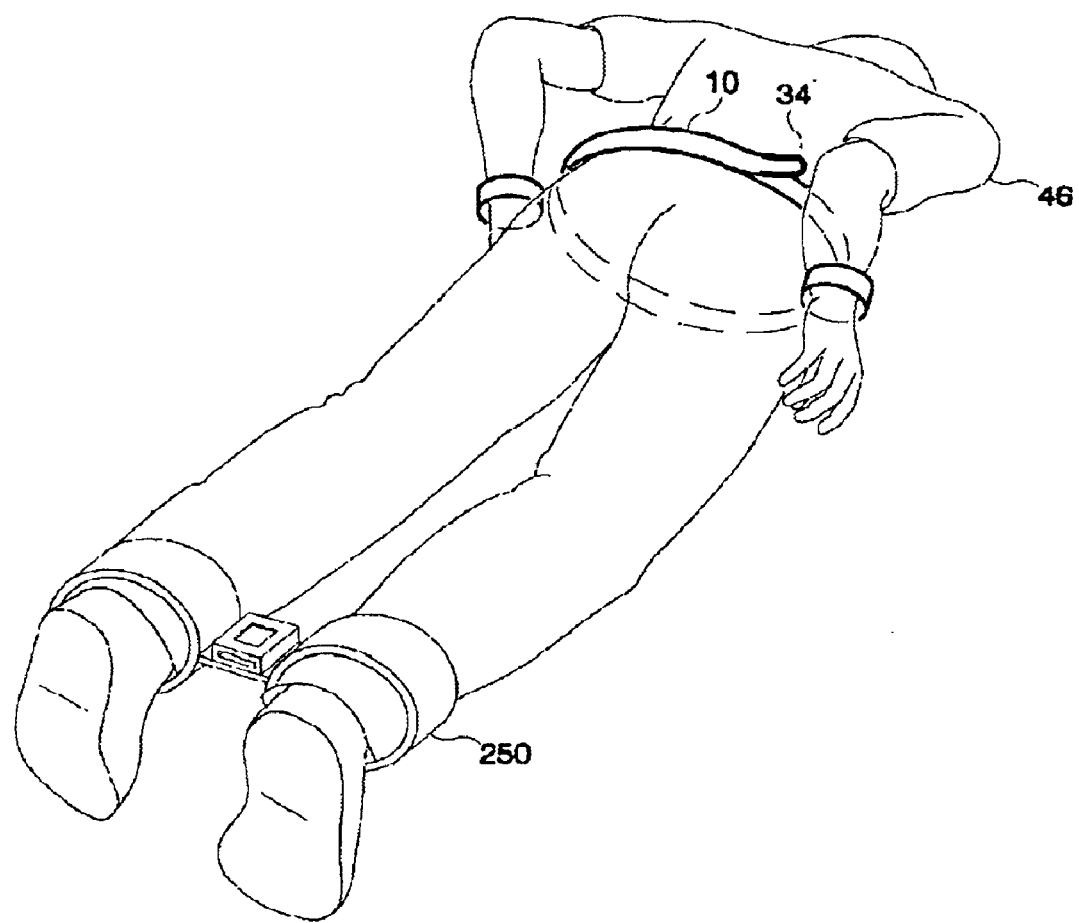
FIG. 5 shows an isometric top view of the arm restraint system of FIG. 1A and the leg restraint system of FIG. 4A advantageously applied to a person in accordance with the present invention.

Referring now to FIG. 5, the EDP is shown in a face down position on a floor surface secured by the arm restraint system 10 and the leg restraint system 250.

In conclusion, the above-described arm and leg restraint systems of the present invention are easy and intuitive to use and inexpensive to manufacture. Finally, the construction of the inventive arm and leg restraint systems makes them easy to deploy in confined areas.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

I claim:

1. A restraint apparatus for restraining a person, comprising:
   a first cuff module to be applied to the person's first limb, said cuff module comprising a first cuff body having a first outer surface, and having first, second and third rigid loops positioned substantially perpendicular to said first outer surface, said second and third rigid loops being positioned proximal to one another and at a first predetermined distance away from said first rigid loop;
   a second cuff module to be applied to the person's second limb, said second cuff module comprising a second cuff body having a second outer surface, and having fourth, fifth and sixth rigid loops positioned substantially perpendicular to said second outer surface, said fifth and sixth rigid loops being positioned proximal to one another and at a second predetermined distance away from said fourth rigid loop;

a first cuff interconnect having a first flat flexible elongated body sized and configured to fit through said first, second, third, fourth, fifth, and sixth rigid loops, and having a first end, a second end, a first top surface and a first bottom surface; and securing means for attaching said first body to said first rigid loop, and when said first and second cuff modules are applied to the person's limbs, threading it through said fourth rigid loop, and then forming:
  a first tension zone at said first cuff module by threading said first body through said second and third rigid loops and then back through said second rigid loop, and
  a second tension zone at said second cuff module by threading said first body through said fifth and sixth rigid loops and then back through said fifth rigid loop, such that said first cuff interconnect is secured around the person's body and said first and second cuff modules are secured to sides of the person's body, so that the range of motion of the person's first and second limbs is significantly restricted.

2. The restraint apparatus of claim 1 wherein said securing means comprises:
  a first connector to connect said first end of said first body to said first rigid loop, wherein said first and second cuff modules are positioned a third predetermined distance apart from one another, and oriented such that said first rigid loop substantially faces said fourth rigid loop, and wherein:
  (1) said second end of said first body is threaded through said fourth rigid loop and folded back toward said first cuff module and then threaded through said second and thud rigid loops,
  (2) said partially folded body is positioned in front of the person's waist and said second end is pulled over the back of the person's waist toward said second cuff module to pull said first and second cuff modules into contact with the sides of the person's waist, and said second end is threaded through said second rigid loop and pulled again toward said second cuff module to create said first tension zone, and
  (3) said second end is threaded through said fifth and sixth rigid loops and then pulled toward said first cuff module to fully secure said first and second cuff modules to the sides of the person's waist, and said second end is threaded through said fifth rigid loop and pulled again toward said first cuff module to create said second tension zone thereby securing said first and second cuff modules to the person's body such that the range of motion of the person's limbs is significantly restricted.

3. The restraint apparatus of claim 2, wherein said third distance is sufficient to encompass approximately one half of the person's waist.

4. The restraint apparatus of claim 1, further comprising: a stiffening element disposed at said second end of said first body to facilitate threading of said second end through at least one of said first, second, third, fourth, fifth and sixth rigid loops.

5. The restraint apparatus of claim 1, further comprising: means for configuring the restraint apparatus for storage and transport.

6. The restraint apparatus of claim 5, wherein said means for configuring further comprises:
  at least one elastic band disposed on said first body between said first end and said first portion of said first body, wherein in a storage and transport configuration said first body is attached to said first rigid loop, threaded through said fourth rigid loop, folded back upon itself at least once, and then stowed under said at least one elastic band.

7. The restraint apparatus of claim 6, wherein said at least one elastic band is secured to one of said first top surface and said first bottom surface.

8. The restraint apparatus of claim 6, wherein said at least one elastic band is disposed around said first body, and is moveable along said first body.

9. The restraint apparatus of claim 1, further comprising a seventh rigid loop disposed on said first body proximal to said securing means and perpendicular to said first body, wherein prior to forming said first tension zone, said second end is threaded through said seventh rigid loop.

10. The restraint apparatus of claim 6, further comprising a first releasable attachment device operable to releasably secure said second end to said securing means when the restraint apparatus is configured for storage and transport.

11. The restraint apparatus of claim 2, wherein said first connector comprises a second releasable attachment device to connect said first end of said first body to said first rigid loop.

12. The restraint apparatus of claim 11, wherein said second releasable attachment device comprises:
  a first elongated loop positioned on said first top surface at a fourth predetermined distance from said first end;
  a second elongated loop positioned next to said first elongated loop on said first top surface at said fourth predetermined distance from said first end;
  a first hole defined proximal to said first end, and a second hole next to said first hole defined proximal to said first end, said first and second holes being positioned and sized such that when said first end is threaded through said first rigid loop in an upward direction and then folded upon itself, said first and second holes are aligned with said first and second elongated loops so that said first and second elongated loops pass through said respective first and second holes to thereby at least temporarily connect said first end of said first body to said first rigid loop;
  a generally U-shaped element having a first segment sized and configured to fit though said first elongated loop once said first elongated loop is passed through said first hole, and a second segment sized and configured to fit though said second elongated loop once said second elongated loop is passed through said second hole;
  a retaining device positioned proximal to said first and second elongated loops that receives and retains said first and said second segments after they are passed through said first and said second elongated loops, wherein when said first end is passed through said first rigid loop and folded back upon itself to pass said first and second elongated loops through said respective first and second holes, said first segment is threaded through said first elongated loop and into said retaining device and said second segment is threaded through said second elongated loop and into said retaining device, to thereby releasably secure said first end to said first rigid loop.

13. The restraint apparatus of claim 12, wherein said retaining device further composes a guide device disposed within said retaining device, that guides said first and said second segments into said retaining device.

14. The restraint apparatus of claim 12, further comprising: a first ring positioned and configured to reinforce said first hole, and a second ring positioned and configured to reinforce said second hole.

15. The restraint apparatus of claim 12, wherein said U-shaped element is selected from a group consisting of: a wire, a plastic member, and a wire coated with a resilient material.

16. The restraint apparatus of claim 1, wherein:
said first cuff module further comprises:
a first cuff segment terminating in a first rigid element, and an eighth rigid loop, positioned proximal to said second and third rigid loops sized and configured to pass said first cuff segment and said first rigid element therethrough, wherein when said first cuff module is applied to one limb, said first rigid element is threaded through said eighth rigid loop and tightened; and
said second cuff module further comprises:
a second cuff segment terminating in a second rigid element, and a ninth rigid loop, positioned proximal to said fifth and sixth rigid loops, sized and configured to pass said second cuff segment and said second rigid element therethrough, wherein when said second cuff module is applied to the other limb, said second rigid element is threaded through said ninth rigid loop and tightened.

17. The restraint apparatus of claim 16, wherein said first rigid element comprises a first releasable connector configured to releasably connect to a first external restraint device, and wherein said second rigid element comprises a second releasable connector configured to releasably connect to a second external restraint device.

18. The restraint apparatus of claim 1, further comprising:
a third cuff module to be applied to the third limb of the person;
a fourth cuff module to he applied to the fourth limb of the person;
a second cuff interconnect having a second flat flexible elongated body of a first length having a third end and a fourth end;
a second connector for attaching said third end to said third cuff module,
a third connector for attaching said fourth end to said fourth cuff module; and
a third releasable connector, positioned between said third and said fourth end, and facing perpendicular to said second body, configured to releasably connect to a third external restraint device.

19. The restraint apparatus of claim 18, wherein said second connector comprises a fourth releasable connector that releasably connects to said third cuff module, and wherein said third connector comprises a fifth releasable connector that releasably connects to said fourth cuff module.

20. The restraint apparatus of claim 18, further comprising pivotable connection means for connecting said third releasable connector to said second body, such that said third releasable connector may be oriented to point in any direction substantially perpendicular to said second body.

21. The restraint apparatus of claim 19, wherein said pivotable connection means is positioned at an approximate midpoint of said second body between said third end and said fourth end.

22. The restraint apparatus of claim 18, further comprising at least one tensioning device positioned along said second body to change said first length of said second body and thus a distance between said third and fourth cuff modules.

23. A restraint apparatus for restraining a person, comprising:
a first cuff module to be applied to a first limb of the person;
a second cuff module to be applied to a second limb of the person;
a cuff interconnect having a flat flexible elongated body of a predetermined length having a first end and a second end;
a first connector for attaching said first end to said first cuff module;
a second connector for attaching said second end to said second cuff module;
a first releasable connector, positioned between said first and said second end, and facing perpendicular to said elongated body, configured to releasably connect to an external restraint device; and
pivotable connection means for connecting said first releasable connector to said elongated body, such that said first releasable connector may be oriented to point in any direction substantially perpendicular to said elongated body.

24. The restraint apparatus of claim 23, wherein said first connector comprises second releasable connector that releasably connects to said first cuff module, and wherein said second connector comprises a third releasable connector that releasably connects to said second cuff module.

25. The restraint apparatus of claim 23, further comprising at least one tensioning device positioned along said elongated body to change said predetermined length of said elongated body, and thus a distance between said first and second cuff modules.

26. A method for restraining a person by applying restraints to at least one limb of a person, comprising the steps of:
(a) providing:
a first cuff module to be applied to the person's first limb, said cuff module comprising a first cuff body having a first outer surface, and having first, second and third rigid loops positioned substantially perpendicular to said first outer surface, said second and third rigid loops being positioned proximal to one another and at a first predetermined distance away from said first rigid loop,
a second cuff module to be applied to the person's second limb, said second cuff module comprising a second cuff body having a second outer surface, and having fourth, fifth and sixth rigid loops positioned substantially perpendicular to said second outer surface, said fifth and sixth rigid loops being positioned proximal to one another and at a second predetermined distance away from said fourth rigid loop, and
a first cuff interconnect having a first flat flexible elongated body sized and configured to fit through said first, second, third, fourth, fifth, and sixth rigid loops, and having a first end, a second end, a first top surface and a first bottom surface; and
(b) attaching said first body to said first rigid loop;
(c) threading said first body through said fourth rigid loop;

(d) applying said first and second cuff modules to the person's limbs; and (e) securing said first and second cuff modules to the person's body by forming a first tension zone at said first cuff module by threading said first body through said second and third rigid loops and then back through said second rigid loop, and forming a second tension zone at said second cuff module by threading said first body through said fifth and sixth rigid loops and then back through said fifth rigid loop, such that said first cuff interconnect is secured around the person's body and said first and second cuff modules are secured to sides of the person's body, so that the range of motion of the person's first and second limbs is significantly restricted.

27. The method of claim 26, wherein:

said step (b) comprises the step of:

(f) providing a first connector to connect said first end of said first body to said first rigid loop, and said step (d) further comprises the step of:

(g) applying said first and second cuff modules to the person's limbs, such that said first and second cuff modules are oriented toward one another so that said first rigid loop substantially faces said fourth rigid loop.

28. The method of claim 27, wherein said step (e) comprises the steps of:

(h) threading said second end of said first body through said fourth rigid loop;

(i) folded said second end back toward said first cuff module;

(j) threading said second end through said second and third rigid loops, (k) positioning said partially folded body in front of the person's waist;

(l) pulling said second end over the back of the person's waist toward said second cuff module to pull said first and second cuff modules into contact with the sides of the person's waist;

(m) creating said first tension zone by threading said second end through said second rigid loop and pulling again toward said second cuff module;

(n) threading said second end through said fifth and sixth rigid loops;

(o) pulling said second end toward said first cuff module to fully secure said first and second cuff modules to the sides of the person's waist, (p) creating said second tension zone by threading said second end through said fifth rigid loop and pulling again toward said first cuff module to thereby secure said first and second cuff modules to the person's body such that the range of motion of the person's limbs is significantly restricted.

29. The method of claim 26, further comprising the steps of:

(q) providing a third cuff module to be applied to the third limb of the person; a fourth cuff module to be applied to the fourth limb of the person; a second cuff interconnect having a second flat flexible elongated body of a first length having a third end and a fourth end; a second connector for attaching said third end to said third cuff module; a third connector for attaching said fourth end to said fourth cuff module; and a releasable connector, positioned between said third and said fourth end, and facing perpendicular to said second body, configured to releasably connect to an external restraint device; and (r) applying said third cuff module to the third limb and applying said fourth cuff module to said fourth limb.

30. The method of claim 29, further comprising the step of:

(s) connecting said releasable connector to said external restraint device.

* * * * *